United States Patent [19]

Vila Peris et al.

[11] Patent Number: 4,754,090
[45] Date of Patent: Jun. 28, 1988

[54] PROCESS FOR THE PREPARATION OF HEXAMETHYL TETRACOSANES

[75] Inventors: José María Vila Peris; Miguel de los Santos Alamany Soler; Roberto Celades Colom, all of Barcelona, Spain

[73] Assignee: Hispano Quimica S.A., Spain

[21] Appl. No.: 947,593

[22] Filed: Dec. 30, 1986

[30] Foreign Application Priority Data

Jan. 4, 1986 [ES]  Spain .................................. 550683

[51] Int. Cl.$^4$ ................................................ C07C 1/00
[52] U.S. Cl. .............................. 585/240; 260/397.25; 585/264; 585/310; 585/733; 585/947
[58] Field of Search .................... 260/397.25; 585/240, 585/264, 733, 947, 310

[56] References Cited

U.S. PATENT DOCUMENTS

| | | | |
|---|---|---|---|
| 3,653,842 | 4/1972 | Putman | 260/425 |
| 3,859,374 | 1/1975 | Komatsu et al. | 585/16 |
| 3,923,918 | 12/1975 | Nishida et al. | 585/733 |
| 3,981,930 | 9/1976 | Nishida et al. | 585/733 |
| 4,011,277 | 3/1977 | Nishida et al. | 585/934 |
| 4,026,960 | 5/1977 | Nishida et al. | 585/16 |
| 4,101,599 | 7/1978 | Debande et al. | 585/277 |
| 4,107,225 | 8/1978 | Debande et al. | 585/277 |
| 4,549,990 | 10/1985 | Sequin et al. | 260/397.25 |

*Primary Examiner*—Curtis R. Davis
*Attorney, Agent, or Firm*—Scully, Scott, Murphy & Presser

[57] ABSTRACT

A process for the preparation of 2,6,10,15,19,23-hexamethyl tetracosane and the isomers thereof having a basic hexamethyl tetracosane structure is described. Therein the raw materials are vegetable triglyceride oils and fats or oleins thereof obtained by physical refining. Together with an optional prior refining step, the process comprises a fatty acid and unsaponifiable material separation step, a saponification step giving unsaturated hydrocarbons, a hydrogenation step and a final deparaffining and purification step.

19 Claims, No Drawings

PROCESS FOR THE PREPARATION OF HEXAMETHYL TETRACOSANES

BACKGROUND OF THE INVENTION

1. Field of the Invention

The invention relates to a process for the preparation of 2,6,10,15,19,23-hexamethyl tetracosane and isomers thereof having a hexamethyl tetracosane structure from certain vegetable fats and oils.

2. Description of the Prior Art

Hexamethyl tetracosanes are derivatives of 2,6,10,15,19,23-hexamethyl-2,6,10,14,18,22-tetracosahexene, a naturally occurring isoprenoid hydrocarbon, of the terpene series. It is, to be precise, a triterpene.

A technical grade thereof, from animal source, was isolated in 1906 from the unsaponifiable matter of shark liver oil. The hydrogenated 2,6,10,15,19,23-hexamethyl tetracosane was obtained in 1923 and the structure was defined in 1929.

The technical grade of animal source hexamethyl tetracosahexene, obtained from shark liver oil, has a strong fish odour and is chemically unstable due to its high degree of unsaturation (iodine number 370), is easily oxidised (becomes stale) and has a tendency to polymerise or "dry out", providing viscous products or even skins.

Due to the above, it was hitherto not possible to use hexamethyl tetracosahexene of animal source, independently of the minor components and impurities from said origin, directly in cosmetics or other applications (lubricants, dielectric fluids, heat transmission fluids, etc.), it having been necessary to hydrogenise it completely prior to use. The hexamethyl tetracosane thus obtained is very stable chemically, has no odour and is fully compatible with the skin. Use of the technical grade of animal hexamethyl tetracosane started in 1950 and has continued down to the present time, the use having grown considerably.

All the naturally occurring hexamethyl tetracosane is currently being obtained from shark liver oil which, owing to the insufficient number of catches and notwithstanding the animal origin of the technical grade and the impurities or minor components involved therewith, causes powerful tensions in the market, caused by the imbalance between a short-falling, irregular supply, against a constantly increasing demand.

SUMMARY OF THE INVENTION

The invention provides a new process for the preparation of this basic product, although based on a technical grade of exclusively vegetable origin, still unknown on the market, such as is the vegetable triglyceride oils and fats or the oleins resulting from the physical refining thereof. The hexamethyl tetracosahexene content of vegetable oils, forming part of the unsaponifiable material thereof, may vary between broad limits, for example, the yeast fats may contain up to 16.3% of this product, rice husk oils 0.3% and olive oils and olive marc 0.7%.

When said crude or raw vegetable oils are refined to remove the acidity therefrom, and other impurities conferring undesirable colours, tastes and odours, for both food use and other industrial applications, consisting usually of a prior purification or demucilagination, chemical buffering with alkaline agents, decolouring with activated materials (activated earths and carbons) and deodorisation with steam stripping, it is not possible to recover the hexamethyl tetracosahexenes from the unsaponifiable material lost with the different by-products resulting from each of the above mentioned ordinary or also so-called traditional refining steps.

The invention clearly shows that if it is wanted to extract the hexamethyl tetracosahexenes, it is necessary to avoid subjecting the crude vegetable oils and fats to an ordinary or traditional refining wherein the acidity is buffered chemically, producing the so-called soapstocks, but it is necessary to remove the acidity by steam stripping or the so-called buffering-deodorising operation which, with the remaining operations required, forms the so-called "physical refining", such that, in practice this operation is performed fundamentally by subjecting the crude vegetable oils and fats to a treatment with activated earths and thereafter to the buffering-deodorization operation.

The hexamethyl tetracosahexene present during the physical refining of said oils, is concentrated in the distillate of the buffering-deodorization operation, together with the fatty acids.

This is so because the vapour tensions of the hexamethyl tetracosahexenes are only slightly higher than those of the higher fatty acids, as may be observed from the fact that at a vapour pressure of 5 mm Hg, palmitic, palmito-oleic, stearic, oleic, linoleic, linolenic, arachidic and erucic acid boil between 180° C. and 245° C., while the hexamethyl tetracosahexenes in question boil between 230° C. and 260° C.

Since the acidity of raw vegetable oils and fats is variable and increases with the time in storage and other factors and the unsaponifiable matter content is fairly constant, the hexamethyl tetracosahexene content in the physically refined oleins thus obtained is generally proportionally inverse to the acidity of the oil to be refined, and may vary between 1% and 30% or even more.

Hereinafter there is described the process for extracting 2,6,10,15,19,23-hexamethyl-2,6,10,14,18,22-tetracosahexene or isomers thereof having a basic hexamethyl tetracosahexene structure and obtaining 2,6,10,15,19,23-hexamethyl tetracosane or isomers thereof having a basic hexamethyl tetracosane structure, as well as derivatives having a degree of unsaturation intermediate the two basic structures cited, i.e. hexamethyl tetracosenes. Since this range of products is of vegatable origin, they offer the same or even greater advantages in cosmetics application than the products derived from shark, liver or other animal sources.

The basic starting raw material, as said above, is constituted by the acid oils and triglyceride fats of vegetable origin and the fatty acids thereof produced by physical refining, acid oils formed by physical refining, or buffering deodorization condensates.

The properties of these oleins vary, for one same physical buffering or buffering deodorization plant, depending mainly on the natural acidity of the crops of oleaginous fruits, on the conditions under which the oils and fats have been obtained from the corresponding fruits and even on the soils and places of origin of the fruits. Generally speaking, when referring for example to olive oil, they may be said to be composed of:

saponifiable material: 70–92%, formed mainly by fatty
   acids and by mono, di and triglycerides which have
   been mechanically stripped off with the vapours.
unsaponifiable material: 7–30%

In turn the unsaponifiable material comprises:

saturated hydrocarbons: 1–3%
unsaturated hydrocarbons: 75–90%
alcohols and polar compounds (straight chain alcohols, terpenes, tocopherols, beta-sitosterol, etc): 5–20%

The unsaturated hydrocarbons are formed, to a great extent, by 2,6,10,15,19,23-hexamethyl-2,6,10,14,18,22-tetracosahexene, such that the content of this compound in the unsaponifiable material is 70–90%, leading to a 7 to 27% content of this product in the physically refined fatty acids, the great majority of the samples analysed giving 10% to 15%.

The process according to the invention is characterised in that condensed oleins of vegetable origin comprising a mixture of unrefined free fatty acids and unsaponifiable material are subjected to: a first step in which they undergo a separation process resulting in the substantial separation of, on the one hand, the fatty acids and, on the other hand, a concentrated residue of hexamethyl tetracosahexene-containing matter; a second step in which the fatty matter still remaining in the concentrated residue is saponified, resulting in the separation thereof and the preparation of technically pure hexamethyl tetracosahexenes, together with other unsaturated compounds; a third step consisting of a hydrogenation process whereby, on the one hand, 2,6,10,15,19,23-hexamethyl tetracosane and isomers thereof having a basic hexamethyl tetracosane structure are obtained from said hexamethyl tetracosahexenes and, on the other hand, there are obtained from said other unsaturated compounds paraffins and other saturated compounds; and a fourth step of deparaffining the hydrogenated products obtained in the foregoing step and purification by deodorization.

Therefore, the process of extraction of hexamethyl tetracosahexenes and preparation of a technical quality of hexamethyl tetracosane of vegetable origin proposed herein comprises the following steps:

Possible prior step: subjecting the vegetable oils and fats, with or without prior purification even of activated materials (adsorbent carbons, activated earths, decolourants, etc) to physical buffering or buffering deodorisation, by stripping with steam or a gas inert to the fatty material, or both simultaneously, under high vacuum and high temperature, the condensates of said operation being collected.

1st step: Concentration of hexamethyl tetracosahexenes. There are three variants of this step:

(a) fractionated distillation of the physically refined oleins or of the volatile esters thereof (with short chain alcohols such as methanol, ethanol, propanol or any other conferring sufficient volatility to the thus obtained esters), to separate the fatty acids and concentrate the residue into hexamethyl tetracosahexenes.

(b) Esterification with an alcohol or with a polyol or reaction with mono- or polyphenols, or arylphenols, or alkylarylphenols, or condensation with alkylene oxides to obtain a non-volatile ester derived from the fatty acids present in the physically refined oleins, allowing for separation by distillation of the hexamethyl tetracosahexenes present.

(c) Liquid-liquid extraction, with a polyphase, multi-stage system, operating with both water and organic solvents or both at the same time, with or without the aid of alkaline, hydrotropic, anti-gel or other agents, to obtain the concentration of the hexamethyl tetracosahexenes in one of the phases. Such compounds are non-polar and are separated from the higher fatty acids which, on the contrary, are polar substances, even by the conversion of the latter into their alkaline or other soaps.

2nd step: Saponification of the fatty acids and other fatty materials in concentrate and preparation of the technically pure vegetable source hexamethyl tetracosahexenes.

3rd step: Hydrogenation and preparation of crude vegetable source hexamethyl tetracosenes and hexamethyl tetracosanes.

4th step: Final purification in two consecutive phases:
(a) deparaffining of the product obtained in the 3rd step;
(b) purification of the odorous impurities and other volatiles by deodorization from the hexamethyl tetracosenes and hexamethyl tetracosanes purified by deparaffining in the previous stage.

It should be pointed out that although the complete process of the invention comprises the application of the five stages cited above to the crude vegetable oils and fats, the possible prior step is an operation that has been regularly used in the industrial art of refining edible oils and fats, whereas there is no hearsay or published knowledge that the other four steps 1 to 4, of the process have been industrially worked.

The operating conditions, the process and the properties of the products obtained in each of the steps will now be described.

Prior step: This consists of physically refining the vegetable source crude oils and fats to remove the oleins condensed in the buffering deodorization operation.

This operation is conducted generally at temperatures lying between 200° C. and 240° C. under a reduced pressure of 1 to 3 mm Hg, using steam as stripping vehicle, both saturated and superheated to 300° C.–350° C. The most frequent types of facility used are continuous operation, both with horizontal layers of oil several cm thick or through pipes or plates, under which the steam is bubbled, and with very thin layers of oil which flow over heated or unheated metal surfaces, or spraying over heating coils, etc, such that the steam flows in the opposite direction over the outer surfaces of the thin layers or drops of oil.

1st step: (a) fractionated distillation.

A facility of the type normally used for fractionating fatty acids may be used for the fractionated distillation of the oleins or volatile esters thereof, produced in the physical refining, without any need to modify the design thereof.

In this way, the hexamethyl tetracosahexenes are concentrated in the distillation residue, while the fatty acids or esters thereof are distilled at different temperatures, depending on the molecular weight thereof and the degree of vacuum applied to the system.

Since this process is well known, only orientative operating conditions are cited, which may be easily adapted, with adequate variations, to plants of varying design or even to molecular distillation, flash or thin layer apparatus. The following parameters are cited, therefore, as a guidance:

Vacuum: 1–3 mm Hg
Supply temperature: 240° C.
Reflux ratio: 3 (relative to the distillate).

When operating under these conditions, with an apparatus having 10 theoretical plates, the result is less than 1% of hexamethyl tetracosahexenes in the distillate and more than 60% concentration of said products in the residue.

1—(b) Esterification and concentration

The esterification reaction is conducted by treating the physically refined fatty acids with an alcohol or polyalcohol, such as glycerine, trimethylolpropane, pentaeythrite, propylene glycol, dipropylene glycol, fatty alcohols, or by condensing as mono- or polyphenols, or arylphenols or alkylarylphenols. An oxyalkylenation reaction may be used, treating the physically refined fatty acids with ethylene oxide, propylene oxide, butylene oxide or styrene oxide.

When esterifying with alcohols or polyols, the catalyst may be of an acid nature, such as sulphuric, phosphoric, p-toluene-sulphonic, metasulphonic acid, stannous chloride or others used in the art. The reaction conditions are as follows:

appropriate vacuum and high temperatures (from 150° to 250° C., preferably 220° C.). The reaction time lies between 4 and 8 hours and the yield is from 80–90%, depending on the concentration of volatiles.

The thus obtained ester is treated under appropriate conditions to provide the hexamethyl tetracosahexenes:

vacuum of 10 mm Hg to 0.2 mm Hg, preferably 1 mm Hg, temperatures of 220° to 320° C., preferably 260° to 300° C.

The distillation may be a batch process or continuous, using a film, flash or molecular distillation evaporator.

2—Saponification.

The saponification of the concentrate and decantation of the soaps formed allows all the esters and fatty acids accompanying the hexamethyl tetracosahexenes to be removed.

The concentrate is saponified treating it with a base in presence of water and a hydrotrope and anti-gelling and other agents allowing the aqueous phase to be separated cleanly from the other phase, to be free from unsaponifiable material and preventing the soaps from gelling.

The base may be any alkali metal, alkaline earth metal, ammonium, mono- or polyamine, alkanoamine hydroxide or other compound giving an alkaline reaction.

The hydrotrope and/or anti-gelling agent may be sodium toluene sulphonate, sodium xylene sulphonate, sodium naphthalene sulphonate, lower alcohols having less than 11 carbon atoms such as, preferably, methanol, ethanol, propanols, butanols or the phosphoric esters thereof or of aromatic hydrocarbons or a mixture of any of them.

The reaction conditions are the normal ones for this well known chemical process, the most appropriate being the following:

hydrolysis temperature between 50° C. and 100° C., preferably 95° C.;
reaction time from 30 min. to 5 hours, preferably 1 hour;
decantation temperature between 30° C. and 95° C., preferably 60° C.

Saponification may also be conducted in an anhydrous medium with metallic sodium suspended in benzene, although the process is not recommendable for use on an industrial scale, in view of it being highly dangerous.

3—Hydrogenation.

The product obtained as described above is highly unsaturated, having an iodine number of 350 to 390. For subsequent application, it must be hydrogenated to an iodine number of less than 5, if a product of sufficient quality is required.

Any appropriate catalyst, e.g. platinum, palladium, Raney nickel, copper chromite or mixture or alloys thereof may be used in the hydrogenation process. The conditions are the normal ones for the traditional hydrogenation process.

The reaction conditions will depend on the catalyst chosen. The following are recited as a guidance, without being limitative:

temperature from 20° to 250° C., preferably 130° to 190° C.;
pressure 1 to 30 atmospheres, preferably 3 to 10 atmospheres;
catalyst concentration from 0.1% to 5%.

4 Final purification: Step (a) deparaffining.

The hydrogenated product contains from 2 to 15% of long straight chain paraffins, which crystallise to give a heterogenous appearance to the reaction mass.

Deparaffining may be a two step process. First, low temperature filtration to remove the higher paraffins, followed by treatment with urea to form the urea complexes and thereby remove the paraffin remains that give excessively high haze points to the end product. Under appropriate conditions, the material may be deparaffinised in a single step by formation of the urea complexes of all the paraffins present.

The traditional techniques of deparaffining in solvent medium (hexane, methyl ethyl ketone and others) or deparaffining with zeolites may be used.

Solvent deparaffining will be conducted at temperatures lying between 0 and −50° C., preferably between −10° and −20° C. The product-solvent ratio should be between 2:1 and 0.5:1, preferably 1:1. Filtering will be performed at the crystallisation temperature.

The urea-paraffin complexes are formed by contacting the product obtained with a saturated methanolic or aqueous solution of urea. The reaction temperature may range from 0° to 50° C., preferably 25° to 40° C. The contact time should be all the longer the greater the paraffin content. Finally, the mass is filtered or centrifuged at the complex forming temperature. The product thus obtained must be washed several times in water to remove any methanol or urea that it may contain.

4—Step (b) Deodorization.

This operation may be performed with the same process and equipment as used for the deodorisation of edible oils. That is, steam stripping under high vacuum and temperature, although always at a lower vacuum and temperature to avoid distillation by steam stripping of the hexamethyl tetracosanes.

It is also contemplated that the first and second steps may be conducted simultaneously by complete saponification of the fatty acids with a base in a two phase system, aqueous and organic, from which the hexamethyl tetracosahexenes are recovered, are washed and distilled to obtain said hexamethyl tetracosahexenes.

Furthermore, the invention also contemplates the possibility of deparaffining the hydrogenated products in a zeolite bed.

EXAMPLE 1

The following amounts, as parts by weight, were charged into a reactor equipped with a vacuum system and heating system capable of reaching 220°–230° C.:

| | |
|---|---|
| Physically refined oleins of rice husk oil | 1,000 |
| trimethylolpropane | 120 |
| Stannous chloride | 0.8 |

Heating was effected under vacuum of 5 mm Hg up to 220° C. and these conditions were held for 5 hours, whereby the acidity reached 3% (acid number=6).

The temperature was raised to 280°-300° C. and the vacuum to 1 mm Hg, thereby distilling 95 parts by weight of a clear, limpid yellow product.

The distillate was saponified by treating with the following amounts:

|  | Parts by weight |
| --- | --- |
| Distillate | 95 |
| 20% sodium hydroxyde in water | 42 |
| water | 60 |

The mixture was heated to 90°-95° C. and stirred for one hour.

The mixture was then cooled to 65° C. and 21 parts by weight of isopropanol were added.

It was allowed to rest at 60° C. for 1 hour, followed by decantation.

The upper layer, weighting 60 parts, was washed three times with water at 60° C., was vacuum dried and placed in a hydrogenation reactor.

1.5 parts by weight of Raney nickel were added.

Hydrogenation was effected at 180° C. and 5 atm pressure until the iodine number had fallen to below 5.

The mixture was filtered at 110° C., to eliminate the catalyst.

55 parts by weight of a colourless product were obtained and were dissolved in 80 parts by weight of hexane. The solution was cooled to −20° C. and filtered at that temperature.

The hexane was removed from the filtrate by distillation to give a colourless liquid which was mixed with 30 parts by weight of a saturated solution of urea in methanol at 40° C.

The reaction mass was slowly cooled under stirring down to room temperature, said conditions being held for 3 hours.

The upper phase was removed by decantation and washed three times with water at 50° C.

After drying, 48 g of deparaffinised product were obtained.

Deodorization was effected at 180° C. and 1 mm Hg with the passage of a weak steam stream.

47 parts by weight of a colourless, odourless, tasteless product having a pour point of −60° C. were obtained.

EXAMPLE 2

The following amounts were charged in an esterification reactor:

|  | Parts by weight |
| --- | --- |
| physically refined olive fatty acids | 1,000 |
| trimethylpropane | 120 |
| stannous chloride | 0.8 |

The mixture was heated to 220° C. under 5 mm Hg vacuum and was allowed to react under these conditions for 5 hours to reach less than 3% acidity.

The vacuum was increased to 1 mm Hg and the temperature was progressively increased to 280°-300° C. 195 parts by weight of a limpid product were distilled during this time.

The distillate was saponified treating with sodium hydroxide in the presence of water, in the following amounts:

|  | Parts by weight |
| --- | --- |
| Distillate | 195 |
| 20% sodium hydroxide in water | 85 |
| Water | 125 |

The mixture was heated to 90°-95° C. and stirred for one hour.

It was then cooled to 65° C. and 43 parts by weight of isopropanol were added.

It was allowed to rest at 60° C. for 1 hour, followed by decantation.

The upper layer, weighing 117 parts by weight, was washed with water three times at 60° C., was vacuum dried and hydrogenated in a stainless steel reactor capable of being pressurised.

2.5 parts by weight of Raney nickel were used as catalyst.

Hydrogenation was performed at 5 atm and 180° C., to give an iodine number below 5.

The mixture was filtered at 110° C. to remove the catalyst.

The product obtained was colourless and crystallized at room temperature, taking on a heterogenous appearance, 110 parts by weight were obtained and were dissolved in 165 parts by weight of hexane.

The solution was cooled to −15° C. and was filtered at that temperature.

After removing the hexane by distillation a product was obtained which, after being mixed with 60 parts by weight of a saturated solution of urea in methanol at 40° C., was slowly deparaffinised by cooling the reaction mass slowly under stirring down to room temperature.

The reaction mass was filtered to retain the crystals of the urea complex formed and the filtrate was allowed to rest, after which the upper phase was removed by decantation.

After washing and drying the upper phase, it was deodorised under the usual conditions: 180° C. and 1 mm Hg, with a current of steam. 96 g of colourless, colourless, odourless and tasteless product were obtained, with a pour point below −60° C.

EXAMPLE 3

400 parts by weight of yeast fat containing 15% of unsaponifiable matter were saponified in an open reactor, with stirring, under the following conditions: temperature 90°-95° C. for two hours.

|  | Parts by weight |
| --- | --- |
| Yeast fat | 400 |
| 20% sodium hydroxide in water | 205 |
| Water | 240 |

After saponification, the mixture was cooled to 65° C. and 90 parts by weight of ethyl alcohol were added.

The mixture was allowed to rest for 1 hour at 60° followed by decantation.

The upper layer was washed with water three times at 60° C., dried under vacuum and weighed 170.

Hydrogenation was perfored in a pressurised reactor, using 3.5 parts by weight of copper chromite as catalyst.

Hydrogenation was performed at 220° C. and 10 atmospheres, down to an iodine number below 5.

The catalyst was removed by filtration at 110° C.

The 165 parts by weight obtained were treated with 250 parts by weight of a saturated urea-methanol solution at 55° C.

The reaction mass was cooled slowly with stirring from 55° C. to 20° C. over at least 4 hours.

It was filtered to remove the urea-paraffin complex formed and the filtrate was allowed to rest at room temperature and then decanted.

It was washed several times with water at 50° C. and dried.

125 parts of deparaffinised product were obtained. This was deodorised at 180° C. and 1 mm Hg, by flowing a weak current of steam therethrough.

The product obtained, 123 parts by weight, was colourless, odourless and tasteless, having a pour point below −60° C.

What we claim is:

1. A process for the preparation of 2,6,10,15,19,23-hexamethyl tetracosane and isomers thereof having a basic hexamethyl tetracosane structure, wherein condensed oleins of vegetable origin comprising a mixture of unrefined free fatty acids and unsaponifiables are subjected to: a first step in which there is applied a separation process giving rise to the substantial separation, on the one hand, of the fatty acids and, on the other hand, of a concentrated residue of hexamethyl tetracosahexene containing material, said separation process comprising a conversion of the fatty acids into esters and subsequent fractionated distillation; a second step in which the fatty material still in said concentrated residue is saponified, resulting in the separation thereof and the preparation of technically pure hexamethyl tetracosahexenes, together with other unsaturated products, said saponification process being conducted by treating said concentrated residue with a base selected from the group comprising an alkaline or alkali earth hydroxide, ammonia, mono- or polyamines, alkanolamines or mixtures thereof and in the presence of a hydrotrope selected from the group comprising sodium toluene sulphonate, sodium xylene sulphonate, sodium naphthalene sulphonate, alcohols of less than 11 carbon atoms, phosphoric esters thereof or of aromatic hydrocarbons or mixtures of any of them, all of which provides an aqueous fraction containing saponified fatty acids and other impurities and a non-polar fraction comprising the hexamethyl tetracosahexenes, which is separated by decantation and subsequently washed; a third step consisting of a hydrogenation process, whereby, on the one hand, 2,6,10,15,19,23-hexamethyl tetracosane and the isomers thereof having a basic hexamethyl tetracosane structure are obtained from said hexamethyl tetracosahexenes and, on the other hand, paraffins and other saturated compounds are obtained from said other compounds; and a fourth step of deparaffining the hydrogenated products obtained in the previous step by way of a fractionated crystallisation of the paraffins and saturated compounds, subsequent separation by centrifugation or filtration, and formation of urea complexes which remove the paraffins, and purification by steam stripping under high vacuum and high temperature.

2. The process of claim 1, wherein said condensed oleins of vegetable origin are obtained from unrefined vegetable oils and fats subjected to a physical buffering or buffering deodorisation operation by stripping with a stripping vehicle comprising steam or inert gas under high vacuum, high temperature conditions.

3. The process of claim 2, wherein said vacuum is from 1 to 3 mm Hg, said temperature is between 200° C. and 400° C. and said vehicle is saturated or superheated steam to 300° C. to 350° C.

4. The process of claim 1, wherein said condensed oleins are obtained from the refining of cryptogamic vegetable fats of the yeast family; from ground nut oil; from wheat germ oil; from olive oil; from olive marc oil or from rape seed oil.

5. The process of claim 1, wherein said esters resulting from the conversion of the fatty acids are more volatile than said fatty acids.

6. The process of claim 5, wherein said esters are the methyl, ethyl or propyl esters of the fatty acids to be separated.

7. The process of claim 1, wherein said esters resulting from the conversion of the fatty acids are less volatile than the material comprising said concentrated residue.

8. The process of claim 7, wherein said less volatile esters are obtained by way of one or more of the following compounds: monohydroxylic or polyhydroxylic alcohols or a mixture thereof.

9. The process of claim 8, wherein said compounds are glycerine, trimethylolpropane, hexylene glycol or higher fatty alcohols.

10. The process of claim 7, wherein said less volatile esters are obtained by condensation with alkylene oxide.

11. The process of claim 10, wherein said alkylene oxides are ethylene oxide, propylene oxide, butylene oxide or styrene oxide.

12. The process of claim 7, wherein said distillation is conducted in a single distillation still at a temperature between 200° C. and 300° C. and under a vacuum of 10 to 0.2 mm Hg.

13. The process of claim 1, wherein said first and second steps are conducted simultaneously by total saponification of the fatty acids with a base, in a two phase system, one being aqueous and the other organic, in which the hexamethyl tetracosahexenes are collected, which is washed and distilled, said hexamethyl tetracosahexenes separating therefrom.

14. The process of claim 1, wherein said first and second steps are conducted simultaneously by separation of the unsaponifiables with the application of liquid-liquid extraction techniques in a polyphase multistep system.

15. The process of claim 1, wherein said hydrogenation process is conducted, with or without catalysts, down to an iodine number of below 10, with the consequent at least partial saturation of the hexamethyl tetracosahexenes and conversion of said other unsaturated compounds in paraffins and in saturated compounds.

16. The process of claim 15, wherein said catalysts are selected from the group comprising platinum, palladium, Raney nickel, copper chromite or mixtures and alloys thereof and said hydrogenation is conducted at a temperature of from 20° to 250° C., a hydrogen pressure of from 0 to 30 kg/cm$^2$ and a catalyst concentration of from 0.1% to 5% by weight of the material to be hydrogenated.

17. The process of claim 1, wherein said solvent medium is selected from the group comprising hexane, heptane, methyl ethyl ketone or mixtures thereof, in a solute/solvent weight ratio of 3:1 to 3:0.1, said temperature is from 20° C. to −60° C. and said filtration is effected at the same temperature as the crystallisation temperature.

18. The process of claim 1, wherein said deparaffining is conducted in a single step by formation of urea complexes of said paraffins and subsequent separation.

19. The process of claim 1, wherein said urea complexes are formed using saturated solutions of urea in water or methanol at a temperature of 0° to 50° C.

* * * * *

UNITED STATES PATENT AND TRADEMARK OFFICE
CERTIFICATE OF CORRECTION

PATENT NO. : 4,754,090

DATED : June 28, 1988

INVENTOR(S) : Jose M. Vila Peris, et al.

It is certified that error appears in the above-identified patent and that said Letters Patent is hereby corrected as shown below:

Column 8, lines 45-46: "colourless, colourless" should read as --colourless--

Signed and Sealed this

Twenty-seventh Day of June, 1989

Attest:

DONALD J. QUIGG

Attesting Officer

Commissioner of Patents and Trademarks